(12) United States Patent
Guarnaschelli et al.

(10) Patent No.: US 11,832,663 B2
(45) Date of Patent: Dec. 5, 2023

(54) BREAST CANCER POST TREATMENT SUPPORT GARMENT

(71) Applicant: JNG International LLC, Cincinnati, OH (US)

(72) Inventors: Jessica Guarnaschelli, Cincinnati, OH (US); Dana Reinisch, Los Angeles, CA (US)

(73) Assignee: JNG INTERNATIONAL LLC, Cincinnati, OH (US)

( * ) Notice: Subject to any disclaimer, the term of this patent is extended or adjusted under 35 U.S.C. 154(b) by 291 days.

(21) Appl. No.: 17/121,235

(22) Filed: Dec. 14, 2020

(65) Prior Publication Data

US 2021/0100299 A1   Apr. 8, 2021

Related U.S. Application Data

(63) Continuation-in-part of application No. 16/251,803, filed on Jan. 18, 2019, now Pat. No. 10,863,779,
(Continued)

(51) Int. Cl.
*A41D 13/12* (2006.01)
*A41D 13/05* (2006.01)
(Continued)

(52) U.S. Cl.
CPC ..... *A41D 13/1245* (2013.01); *A41D 13/0053* (2013.01); *A41D 13/0518* (2013.01); *A61K 31/4166* (2013.01); *A61K 31/726* (2013.01); *A61K 33/38* (2013.01); *A61K 36/886* (2013.01); *A61K 47/02* (2013.01); *A61K 47/10* (2013.01);
(Continued)

(58) Field of Classification Search
CPC ............ A41D 13/1245; A41D 13/0053; A41D 13/0518
See application file for complete search history.

(56) References Cited

U.S. PATENT DOCUMENTS 2,522,010 A * 9/1950 Woodruff ................. A41C 3/04
                                                       D2/709
2,679,048 A   5/1954 Alberts
(Continued)

FOREIGN PATENT DOCUMENTS

WO   2017006088 A1   1/2017
WO   2020070141 A1   4/2020

*Primary Examiner* — Gloria M Hale
(74) *Attorney, Agent, or Firm* — THOMPSON HINE LLP

(57) ABSTRACT

A support garment for breast cancer patients who have undergone or are going through radiation therapy after lumpectomy, mastectomy, or breast reconstruction is provided. A garment for a wearer having breasts and an under bust located directly under the breasts can include a head opening, first and second arm openings, a band configured to fit at the under bust of the wearer, and a cup extending from the band. The cup may include an outer layer, an inner layer that is interior to the outer layer, and an attachment component configured to removably couple an insert to the inner layer. The garment may also include the insert removably coupled to the inner layer. When the garment is worn, at least a portion of the insert is exposed to skin of the wearer, and the insert provides topical therapy and cooling to the skin.

19 Claims, 9 Drawing Sheets

Related U.S. Application Data which is a continuation-in-part of application No. 15/653,174, filed on Jul. 18, 2017, now abandoned.

(60) Provisional application No. 62/363,571, filed on Jul. 18, 2016.

(51) Int. Cl.
| | | |
|---|---|---|
| A41D 13/005 | (2006.01) | |
| A61K 33/38 | (2006.01) | |
| A61K 31/726 | (2006.01) | |
| A61K 36/886 | (2006.01) | |
| A61K 47/18 | (2017.01) | |
| A61K 47/32 | (2006.01) | |
| A61K 47/14 | (2017.01) | |
| A61K 47/10 | (2017.01) | |
| A61K 31/4166 | (2006.01) | |
| A61K 47/38 | (2006.01) | |
| A61K 47/02 | (2006.01) | |

(52) U.S. Cl.
CPC ............ *A61K 47/14* (2013.01); *A61K 47/183* (2013.01); *A61K 47/32* (2013.01); *A61K 47/38* (2013.01); *A41D 2300/20* (2013.01); *A41D 2400/32* (2013.01); *A41D 2600/00* (2013.01)

(56) References Cited

U.S. PATENT DOCUMENTS

| | | |
|---|---|---|
| 4,369,792 A | 1/1983 | Miller |
| 10,863,779 B2 * | 12/2020 | Guarnaschelli ...... A41C 3/0014 |
| 2009/0325464 A1 | 12/2009 | Dekoster |
| 2013/0232661 A1 | 9/2013 | Huntley |
| 2015/0071978 A1 | 3/2015 | Chang |
| 2016/0243164 A1 | 8/2016 | Yates et al. |
| 2017/0265530 A1 * | 9/2017 | Donlon ................ A41C 3/0014 |
| 2018/0014579 A1 * | 1/2018 | Gumlaw .................. A41C 3/02 |
| 2019/0159527 A1 | 5/2019 | Guarnaschelli et al. |

\* cited by examiner

BREAST CANCER POST TREATMENT SUPPORT GARMENT

CROSS-REFERENCE TO RELATED APPLICATIONS

This application is a continuation-in-part of U.S. patent application Ser. No. 16/251,803, filed Jan. 18, 2019, now U.S. Pat. No. 10,863,779, granted on Jan. 18, 2019, which is a continuation-in-part of U.S. patent application Ser. No. 15/653,174, filed Jul. 18, 2017, now abandoned, which claims the benefit of U.S. Provisional Application No. 62/363,571, filed Jul. 18, 2016, the disclosures of which are each incorporated herein by reference in its entirety.

TECHNICAL FIELD

Embodiments of the technology relate, in general, to post-surgery and radiation treatment breast support garments and, more specifically, breast support garments for use during or after breast cancer treatments involving radiation therapy.

BACKGROUND

Breast cancer treatments often have deleterious effects on the body. Due to advances in surgery and radiation, treatment techniques and early detection, more and more women are being treated with lumpectomy and radiation therapy instead of a mastectomy. Radiation therapy typically causes significant irritation of the skin in the treated area, which is much akin to a sunburn. The skin may feel raw, blistered, tender, and sensitive to touch, rubbing, movement, or stretching. Often, patients will endure radiation skin peeling, discomfort, and swelling around and within the breast tissue. Patients may have radiation "burns" beneath or around the breast and within the axilla. Also, they may have irritation, peeling, and burning of the nipple and areola. Post-radiation skin may be subject to discomfort, such as by radiation dermatitis, ulcers, weeping, dryness, or inflammation. The treated skin may be at risk of secondary infections. Finally, patients may have lasting heaviness and soreness of the breast from acute and chronic swelling, which may last from 6 weeks to 5 years after radiation treatment.

Topical treatments for radiation dermatitis have been used for many years. Currently, radiation dermatitis is managed by using topical agents such as oils, gels, lotions or sprays. Breast cancer patients are at risk for chronic wound infections. This is especially true post-surgery and in patients who have medical co-morbidities (advanced age, high body mass index, obesity, diabetes, prior chemotherapy, immune suppression). These risk factors may cause prolonged healing times due to the presence of increased bacteria ($>10^5$ colony forming units/g). This burden of increased bacteria prolongs the inflammatory phase of wound healing, inhibits the proliferative phase. Consequently, the third and last phase of wound healing, epithelialization/tissue remodeling, cannot proceed and thus the healing may not conclude. Thus, systemic antimicrobials may be used; however, systemic treatments may result in unintended sequala including poor bioavailability to the wound site. This approach is also problematic with the rise in incidence of superinfections with organisms such as *Candida*, Enterobacteriaceae, or *Pseudomonas* as well as microbial drug resistance leading to MRSA (Methicillin Resistant *Staphylococcus aureus*) and vancomycin-resistant *enterococcus* (VRE).

Depending on the extent and severity of radiation dermatitis, there are many options for management. In addition to the lotions, oils, creams and spray, 1% silver sulfadiazine cream is a commonly used topical antimicrobial treatment for radiation dermatitis. Silver sulfadiazine cream has a hydrophobic base and may cause discomfort and irritation when removed from the application site in between dressings. There is a need for an improved treatment that also addresses the discomfort and pain associated with breast radiation dermatitis.

SUMMARY

In an embodiment, a garment for a wearer having breasts and an under bust located directly under the breasts can include a head opening, first and second arm openings, a band configured to fit at the under bust of the wearer, and a cup extending from the band. The cup may include an outer layer, an inner layer that is interior to the outer layer, and an attachment component configured to removably couple an insert to the inner layer. The garment may also include the insert removably coupled to the inner layer. When the garment is worn, at least a portion of the insert is exposed to skin of the wearer, and the insert provides topical therapy and cooling to the skin.

BRIEF DESCRIPTION OF THE DRAWINGS

The present disclosure will be more readily understood from a detailed description of some example embodiments taken in conjunction with the following figures.

DETAILED DESCRIPTION

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

In various embodiments, improved post-radiation therapy breast support garments are provided that emphasize comfort against the skin of a wearer while providing topical therapy and reduced discomfort.

Figure 1:
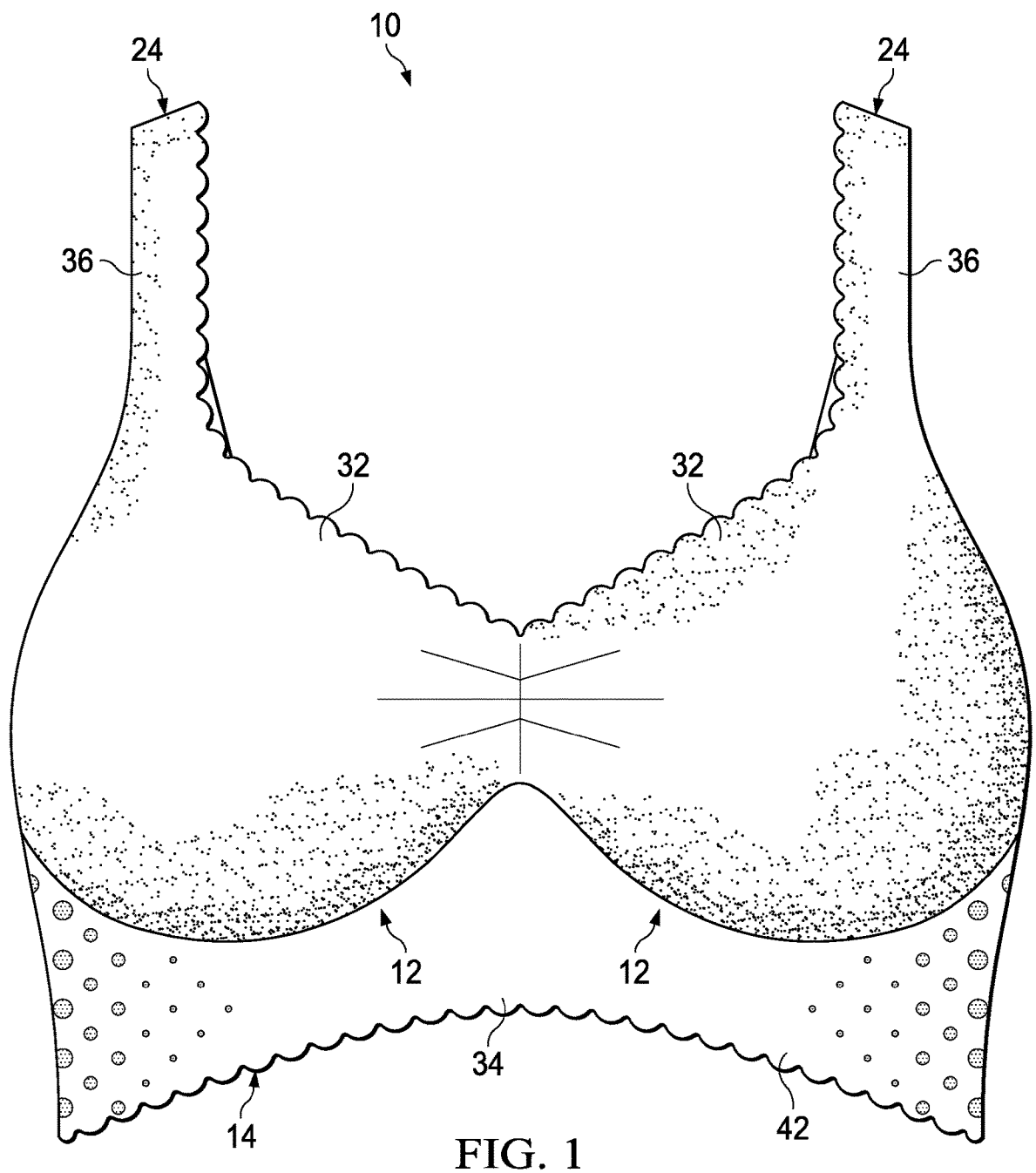
FIG. 1 is a front view of a post-treatment garment according to an embodiment.
Figure 2:
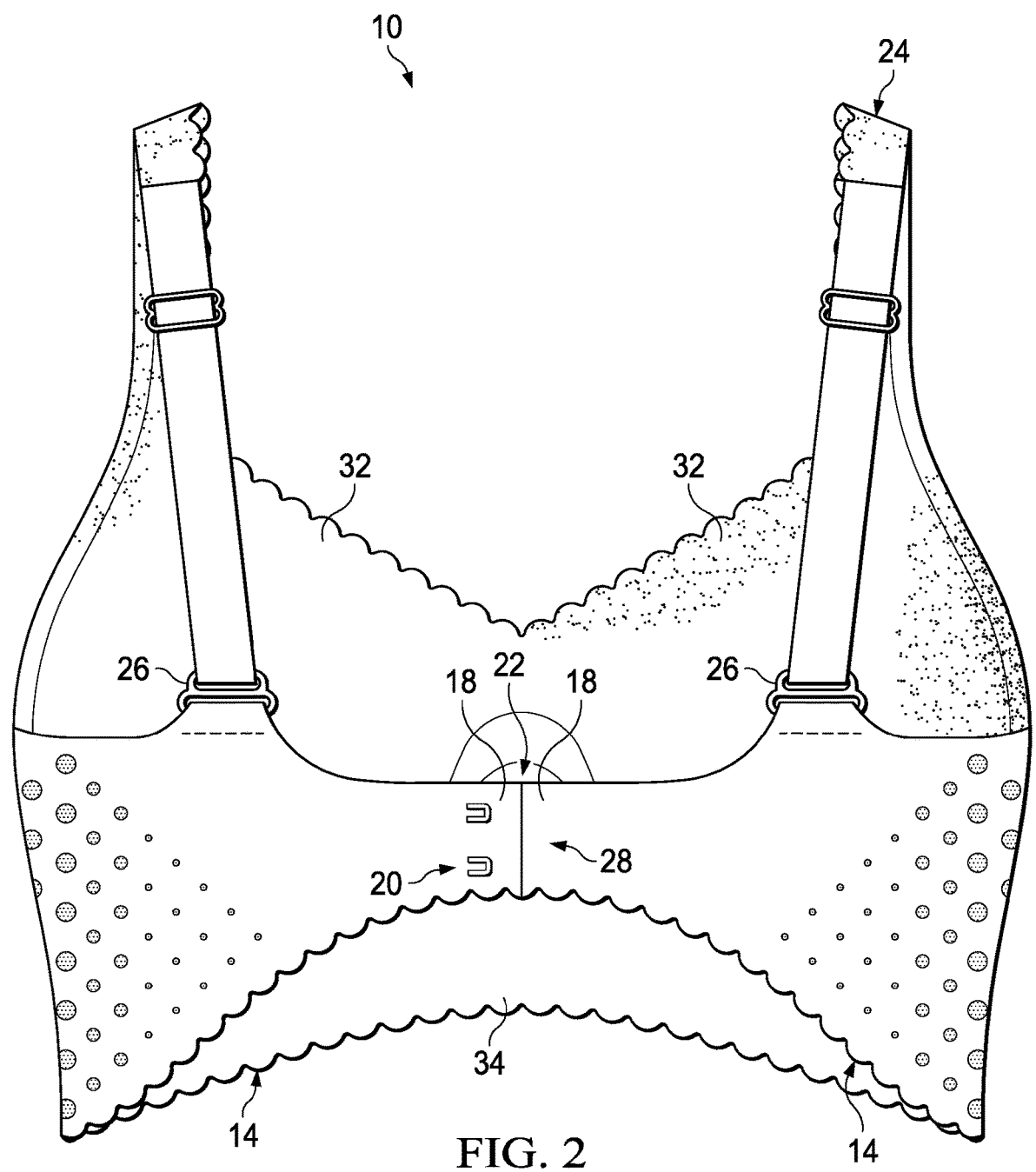
FIG. 2 is a back view of the post-treatment garment of FIG. 1.

With reference to FIGS. 1 and 2, in an embodiment, a post-treatment breast support garment 10 is shown having a head opening and first and second arm openings. The garment 10 includes two cups 12 with ultrasonic welded, cut & sealed edges with foam for supporting the wearer's breasts. Coupled to the cups 12 is a band 14 that extends around a wearer's torso below the bust. The cups 12 may be sewn into the band 14, made of screen-printed silicone flocked standoff texture to reduce chafing inside & out. When worn, the bottom of the cups 12 may rest against the inframammary fold of the breast. For example, the inframammary fold may be about 2 cm lower than the most inferior part of the breast that is flat against the chest wall. The garment 10 can include a soft bonded-in fabric creating a soft, wireless support instead of using an underwire. The molded cups 12 can be attached to the chest band 14 with a pocket to secure a prosthesis with a separate inner most cup fabric coated to provide a pocket for prosthetic breast forms that will be bonded in perimeter only (e.g., between the inner layer and outer layer described below). The garment 10 has a rear closure 16, with a seamlessly integrated one hook & eye with four rows which helps ease any shoulder discomfort that may be present after treatment. The rear closure 16 includes two strips 18 that each extend from the cup 12 towards the bottom of the band 14. Each strip 18 includes a row of closure elements. In the illustrated embodiment, the closure elements include a hook on one of the strips 18 and a corresponding eye with four rows 22 on the other of the strips 18. The hooks 20 may be inserted into the eyelets 22 to secure the garment 10 around the wearer. The rear closure 16 further includes a flap 23 positioned between the closure elements and the skin. The flap 23 prevents the hooks 20 and eyelets 22 from contacting the skin. While the illustrated embodiment depicts a rear closure, it should be recognized that the garment 10 may include a front closure. The garment 10 further includes two straps 24 that are coupled to the top of the cups 12 via hooks 26. The straps 24 extend from the top of the cups 12, over the wearer's shoulders, and towards the back of the band 14. The straps 24 are relatively wide (e.g., compared to an average bra strap width) to disperse the load. The length of the straps 24 may be adjustable.

Figure 3:
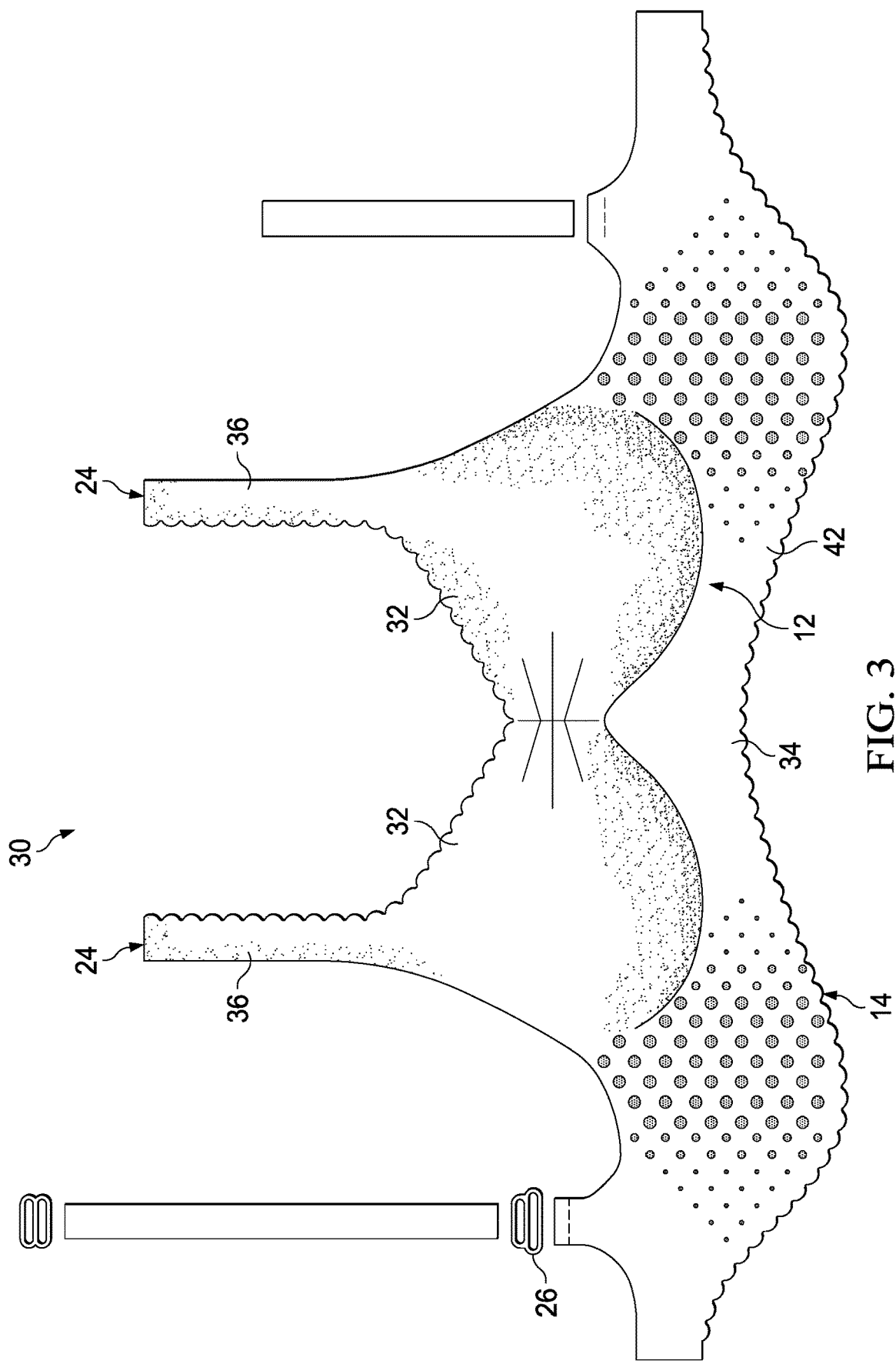
FIG. 3 is a front view of a post-treatment garment according to an embodiment.
Figure 4:
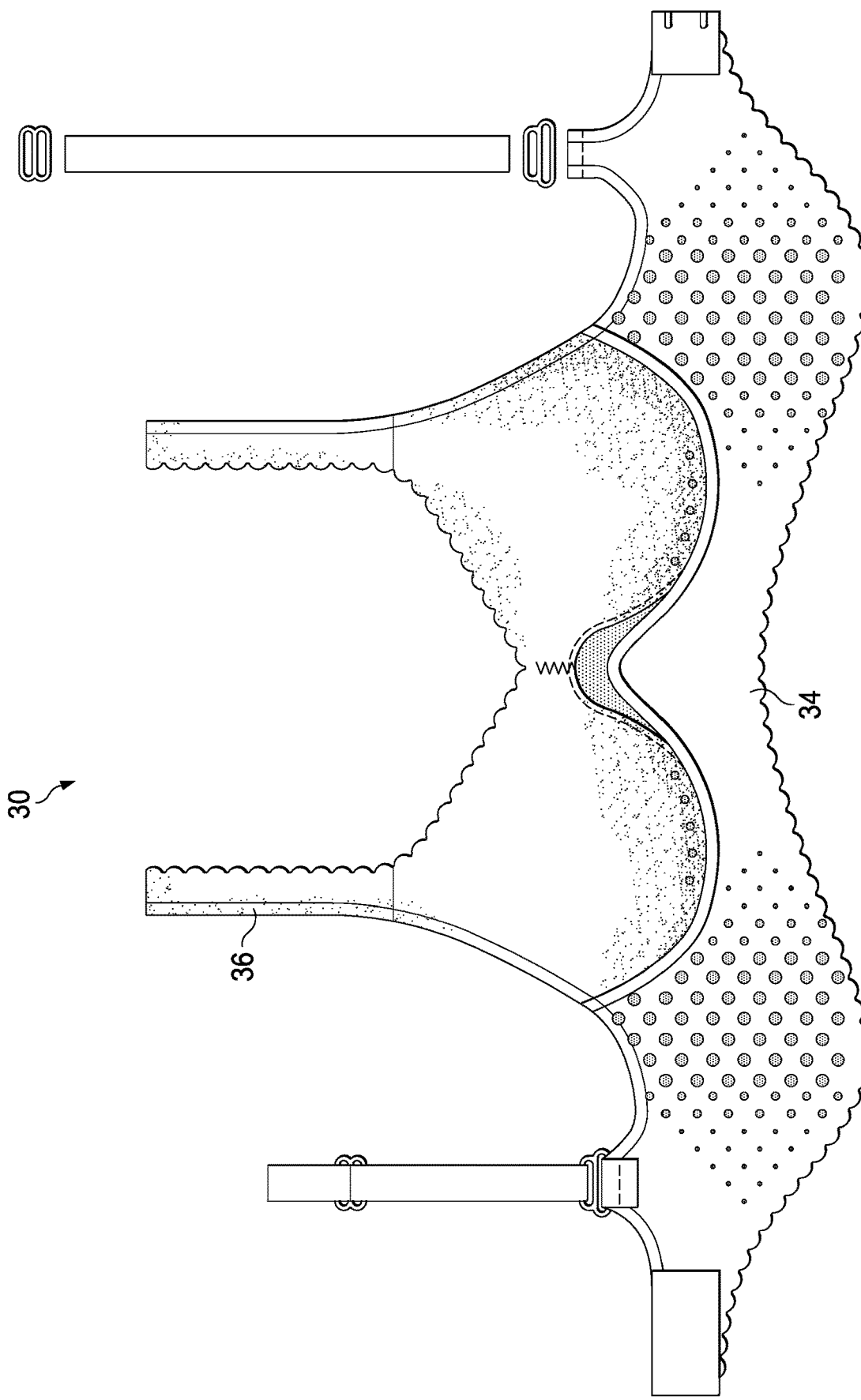
FIG. 4 is a back view of the post-treatment garment of FIG. 3.

With reference to FIGS. 3 and 4, in an embodiment, a post-treatment breast support garment 30 is shown having a head opening and first and second arm openings. Similar to the garment 10, the garment 30 includes two cups 32 for supporting the wearer's breasts. Coupled to the cups 32 is a band 34 that extends around the wearer's torso below the bust. The garment 30 further includes straps 36 that are integrally formed with the cups 32. The straps 36 extend over the shoulders of the wearer and form a racer-back shape. It should be recognized that the straps may be made in a shape other than T-shape or racer-back as long as the straps are wide enough to provide adequate support to the cups. Like the garment 10, the garment 30 has a rear hook-and-eye closure 28, which includes hooks 20, eyelets 22, and the flap 23.

Figure 5:
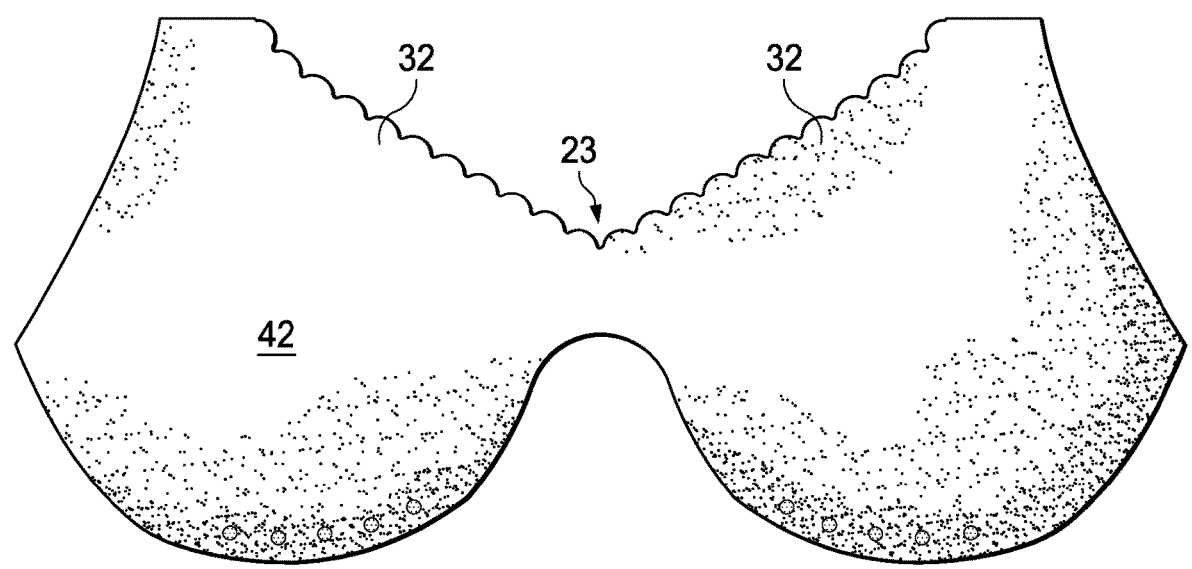
FIG. 5 is a partial view of the back of the post-treatment garment of FIG. 3.

Referring now to FIG. 5, the garment 30 of FIGS. 3 and 4 is shown in more detail. However, these features equally apply to the garment 10 of FIGS. 1 and 2. The cups 32 include an outer layer, whiCh may be the same as the material used to form the straps 36 and/or the band 34. The material forming the band 34, straps 36, and outer layer of the cups 32 should be soft, able to wick moisture away from the skin, and elastic so the garment 30 stretches with the movements of the wearer. Further, the material may be hypoallergenic to reduce the likelihood of irritating the skin and include holes cut out by laser or die cut in the coated fabric for breathability and moisture management. The material may include, for example, about 70-80% bamboo viscose, about 10-30% polyamide, and about 5-20% elastane. Other exemplary materials include organic cotton, spandex, and satin. The cups 32 further include an inner layer 42 that is soft to avoid irritating the sensitive skin affected during treatment. For example, the inner layer 42 may be made of satin or ribbed microtexture fabric that reduces chafing of the irradiated skin. The garment 30 may be configured to reduce chafing at the axilla and along the band 34. For example, the soft inner layer 42 may extend from the inside of the cups 32 along an inner surface of the band 34 and fold out above an outer surface of the band 34 (shown in FIG. 3). For example, the folded material may cover portions of the outer surface of the band 34 that are likely to be in contact with skin (e.g., the axilla, arm). An edge of the folded material from layer 42 may extend along the outer surface of the band 34 to a bottom edge of the cups 32 to act as a soft, wireless support (e.g., instead of including an underwire).

Figure 8:
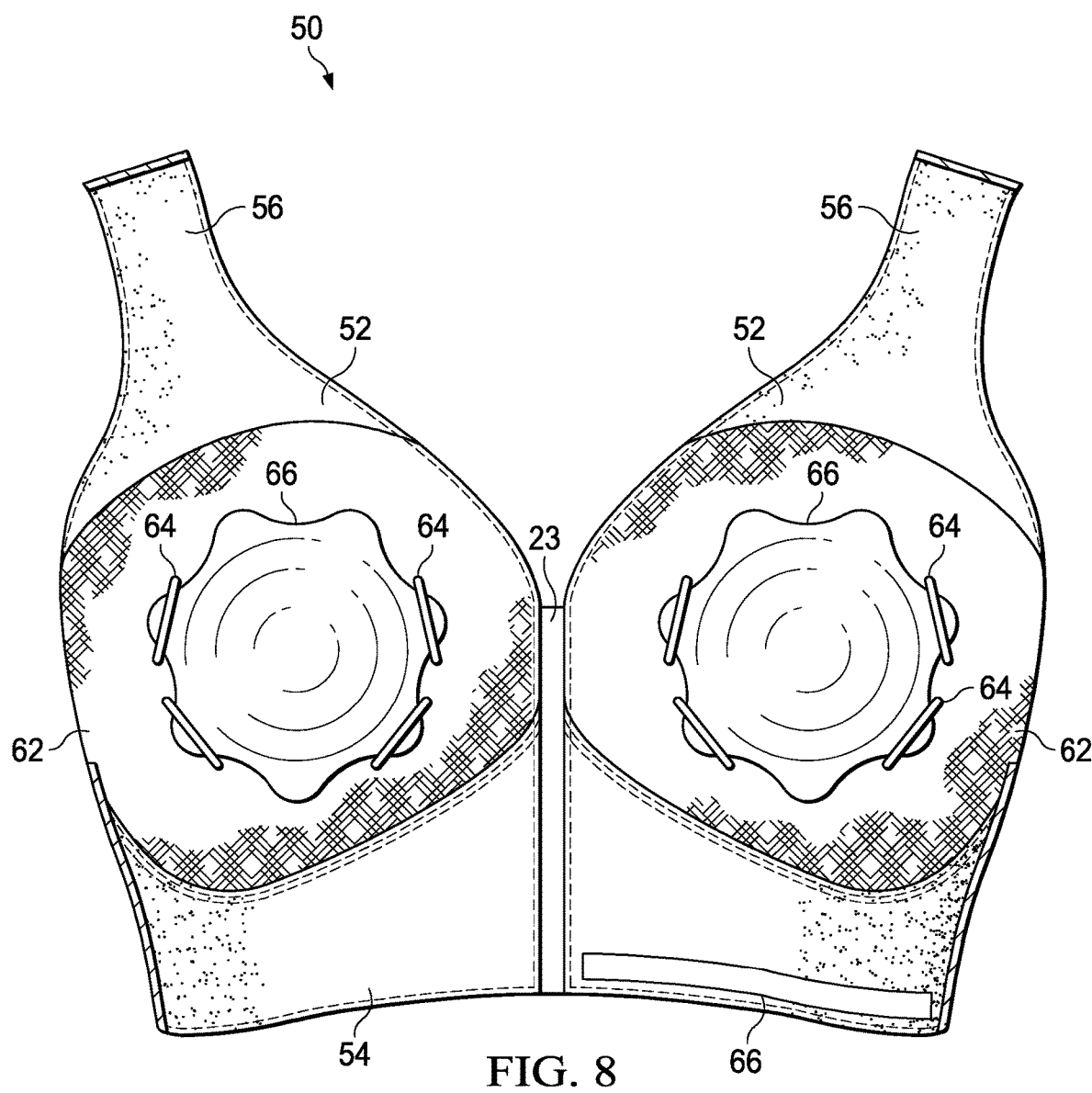
FIG. 8 is a cross-sectional view from the back of the post-treatment garment of FIG. 6.
Figure 9:
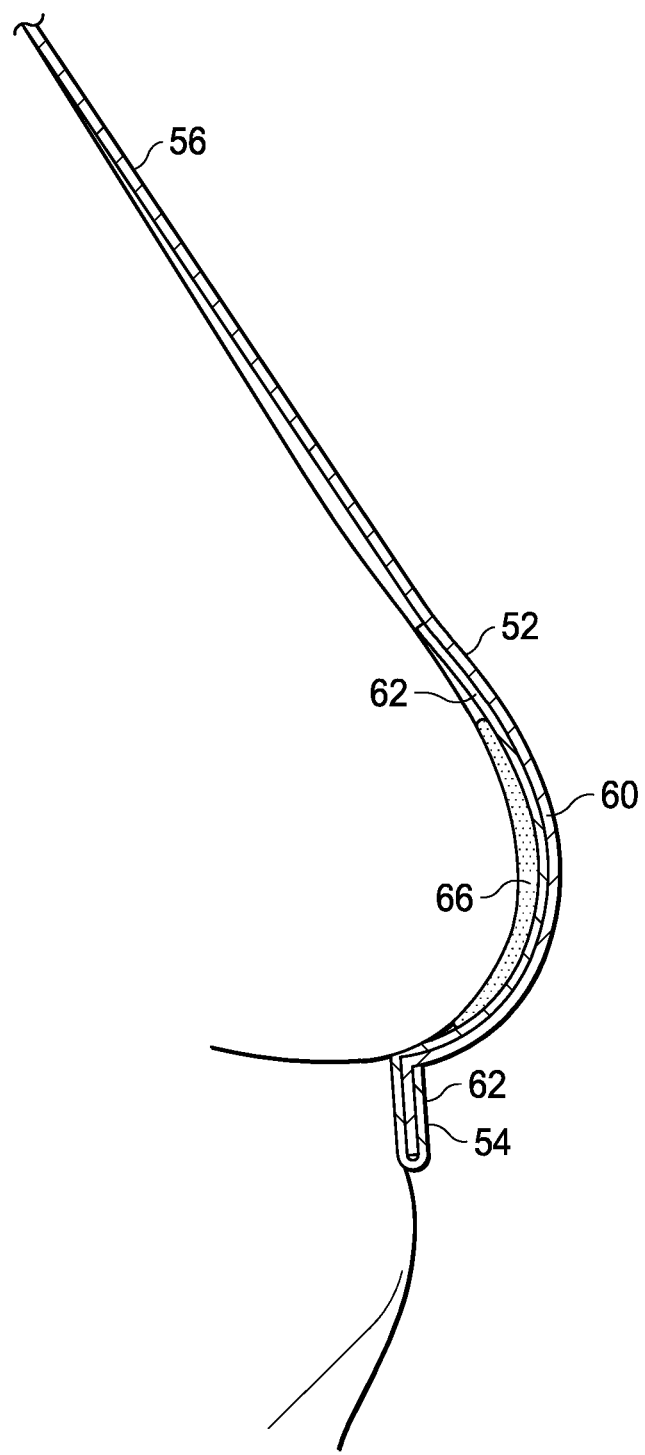
FIG. 9 is a cross-sectional view from the side of the post-treatment garment of FIG. 6.

With reference to FIGS. 6-9, in an embodiment, a post-treatment breast support garment 50 is shown having a head opening and first and second arm openings. Similar to garments 10, 30, the garment 50 includes two cups 52 for supporting the wearer's breasts. Coupled to the cups 52 is a band 54 that extends around the wearer's torso below the bust. The garment 50 further includes straps 56 that are integrally formed with the cups 52. The straps 56 extend over the shoulders of the wearer and form a racer-back shape. It should be recognized that the straps may be made in a shape other than T-shape or racer-back as long as the straps are wide enough to provide adequate support to the cups. The garment 50 has a rear hook-and-eye closure 58, which includes hooks 20, eyelets 22, and the flap 23. As shown in FIG. 9, an edge of the folded material from layer 62 may extend along the outer surface of the band 54 to a bottom edge of the cups 52 to act as a soft, wireless support (e.g., instead of including an underwire).

Figure 6:
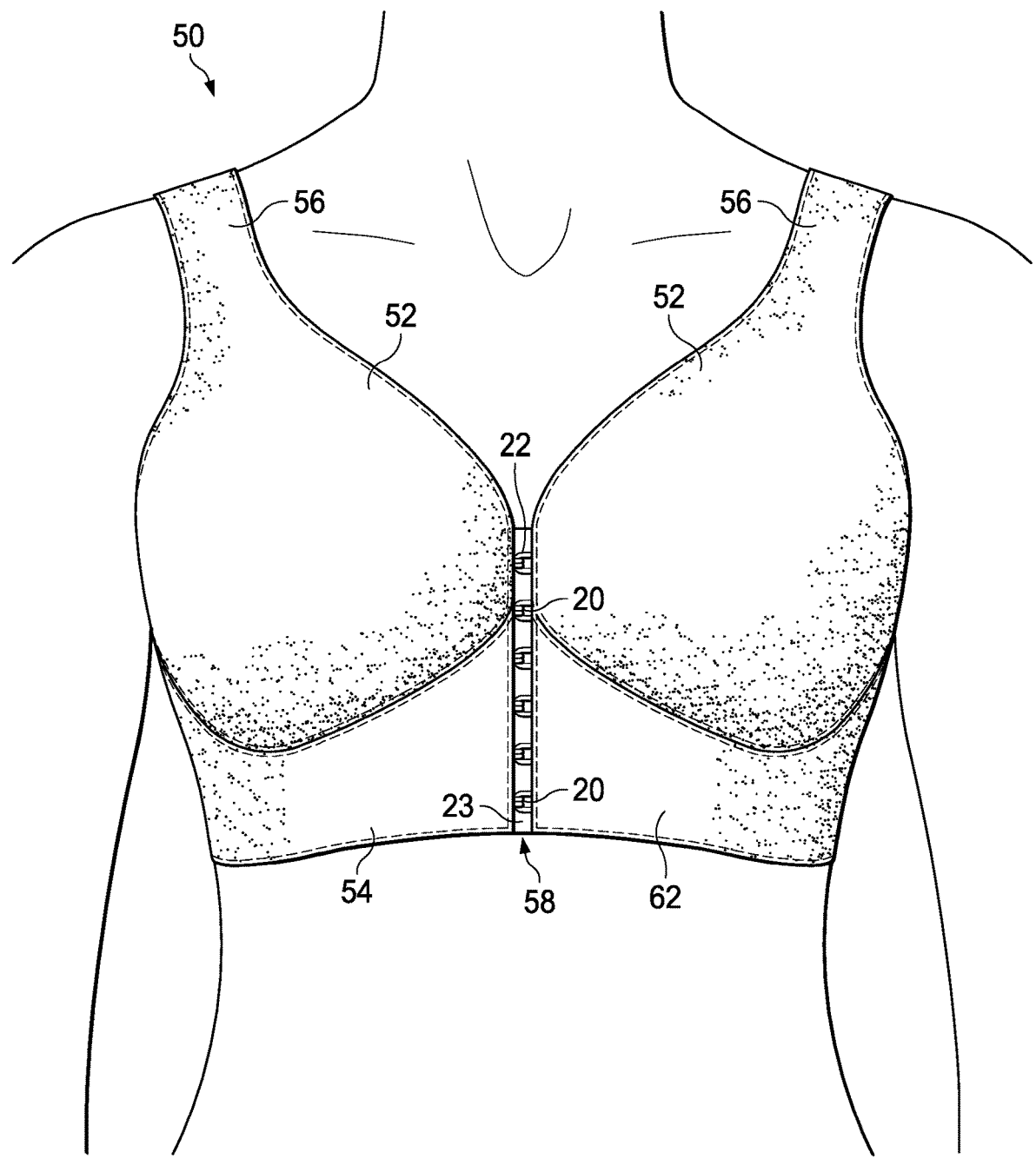
FIG. 6 is a front view of a post-treatment garment according to an embodiment.
Figure 7:
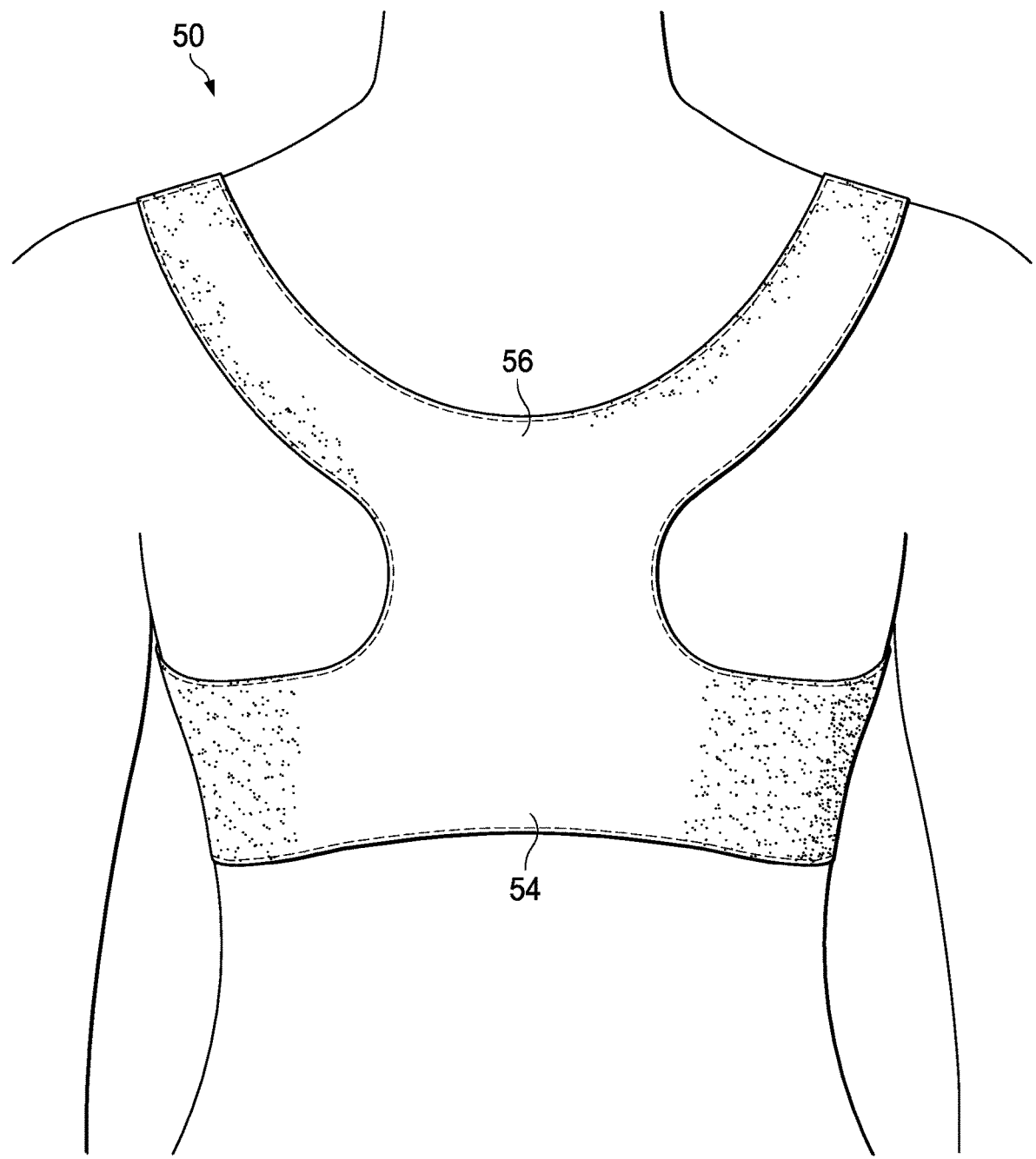
FIG. 7 is a back view of the post-treatment garment of FIG. 6.

As shown in FIGS. 8 and 9, in various embodiments, an insert layer 66 may be removably coupled to each of the cups 52. For example, the insert layers 66 may be removably coupled to the inner layer 62 via an attachment component. In the illustrated embodiment, the attachment component includes a plurality of threads 64 or strings that are attached to the inner layer 62. Corners of the insert 66 may be positioned between the threads 64 and the inner layer 62. When each of the corners is held by a thread 64, the insert 66 is secured to the garment 50. The insert 66 may be made of, for example, a hydrogel. The hydrogel may be a medical grade silicone, such as a Lily Padz silicone pad available from Me & My Kidz, LLC. At least a portion of the insert 66 is exposed so that, when worn, the insert 66 is in contact with the skin. For example, the insert 66 may be in contact with the nipple, areola, and/or axilla area of the breast to ease any discomfort (e.g., burning, peeling, etc.) caused by the treatment. The shape and size of the insert 66 may vary. For example, the shape may have the Lily Padz shape as shown in FIG. 8 or may be, without limitation, circular, rectangular, etc. In various embodiments, the insert 66 may be a 6 cm×6 cm square, a 3 inch diameter circle, or a 4 inch×7 inch rectangle. The wearer may adjust the size of the insert 66 before coupling it to the inner layer 62. The insert 66 provides less irritation to the irradiated skin compared to the material of the inner layer 62. In various embodiments., an insert 66 may be coupled to other portions of the garment 50. For example, an insert 66 may be removably coupled to the inner surface of the band 54 or the inner layer 62 to provide relief to the inframammary fold of the wearer (as shown in FIG. 8). For example, an insert 66 adjacent the inframammary fold may be rectangular. In one or more embodiments, as shown in FIGS. 6 and 9 the inner layer can transition around the front of the garment 50 to be coupled to the outer layer 60 of the cups 52.

In various embodiments, an insert, such as the insert 66, may be used to provide relief or promote healing through contact with the skin. For example, an insert may be act to cool the adjacent skin. In an embodiment, the insert may be removably coupled to the inner layer or may be inserted into a pocket defined at least in part by the inner layer. The portion of the insert that contacts the skin of the wearer is configured to not "stick" to the skin. The insert may provide relief from skin irritation, burning, swelling and expedites healing from radiation skin injury. The insert may be used to relieve pain and discomfort when applied to skin regions injured by radiation dermatitis (e.g., nipple, areola, inframammary fold, and axilla). In some embodiments, the insert may provide topical therapy that has activity against bacteria, *candida*, and viruses that result as secondary infection from radiation injury. An insert may provide both topical therapy and cooling effects.

In some embodiments, the insert may be a hydrogel including one or more active ingredients imbedded into a matrix of polymers to form a cooling, antimicrobial insert. Dermal infections for breast cancer patients who have radiation dermatitis may cause delays in wound healing and increase morbidity after breast surgery and radiation treatments. Postoperative, post-radiation wound complications may range from delayed healing to local and regional dermal infections. Infected wounds disrupt the phases of wound healing by prolonging the inflammatory phase (usually lasting 1-5 days). Once prolonged, the next phase, proliferative phase (usually lasting 3-5 weeks), and final phase, epithelialization/tissue remodeling cannot happen for completion of wound healing. The insert may prevent infections in the affected area from superficial bacteria, fungi, and viruses.

For example, the active ingredient may include one or more antimicrobial agents. An example antimicrobial agent includes medical grade silver salt. The ionic form of silver is antimicrobial, and the principle mechanism of action: ionic silver binding to microbial proteins which result in structural changes within cell walls. Silver binds to DNA and RNA, denatures nucleotides and inhibits replication of cells. The silver salts can be in the anhydrous form (i.e., less than 10% retained water) or hydrous form (i.e., containing greater than 10% water; includes a concentrate). Examples of suitable silver salts include, but are not limited to, silver nitrate, silver dihydrogen citrate, silver citrate, silver chloride, silver benzoate, silver acetate, silver galacturonate, silver glucoronate, and combinations thereof. The concentration of ionic silver as a salt may be in a range of about 5 ppm to about 200 ppm. These concentrations of ionic silver in a topical formulation are not considered toxic. It has been demonstrated and is noteworthy that when a wound dressing containing 85 mg/100 cm of ionic silver was applied to the skin of chronic ulcer patients for four weeks, systemic blood levels of silver was not significantly different from controls.

The active ingredient may include, in some embodiments, acemannan. For example, the active ingredient may include *Aloe vera* gel, which includes acemannan. *Aloe vera* gel can be found in the rind of the *Aloe vera* plant by opening an aloe leaf. The *Aloe vera* gel contains a variety of chemical substances with a large molecular weight complex carbohydrate including acemannan. Acemannan is a high molecular weight carbohydrate polymer of the gel and can be separated either by alcohol precipitation, column purification, or ultra-filtration. Among other properties, acemannan has an immunomodulation function. Included as part of the immunomodulation property is the ability to stimulate release of growth factors for expedited wound healing. There is evidence that acemannan may interfere with attachment of bacteria to epithelial cells. Also, there are anti-inflammatory properties that aid in the control of pain from radiation injury. *Aloe vera* cream has been compared to silver sulfadiazine in second degree burn patients and this demonstrated documented improvement in times to epithelialization of the dermis in patients who use *Aloe vera* compared to use of silver sulfadiazine creams. An insert including an aloe extract acemannan gel provides accelerated healing, decreased inflammation, and added pain control. *Aloe vera* gel or its extract, bulk acetylated mannans from *Aloe vera* (acemannan) have not been shown to be toxic or cause allergic reaction at the concentrations used in the present invention and any one of these products would be suitable for use. The *Aloe vera* gel extract may be in an anhydrous form. The concentration of anhydrous *Aloe vera* gel extract acemannan may be in a range of about 0.05 wt % to about 1 wt % of the total weight of active ingredients.

In some embodiments, the active ingredient may include a chelator that acts as a stabilizer for silver salt. For example, the chelator may be a tetra acetic acid compound. Tetra acetic acid chelating compounds include, but are not limited to, ethylenediaminetetraacetic acid (EDTA), ethylene glycol tetra acetic acid (EGTA), and 1,2-bis(o-aminophenoxy) ethane-N,N,N',N'-tetra acetic (BAPTA). Topical exposure of disodium EDTA for up to 4 hours in a human patch test showed no reactivity thus it is an excellent stabilizer for topical products. In addition, it has been shown that EDTA in conjunction with a silver salt, more specifically silver nitrate, significantly increased the antibacterial action of the silver. The concentration of the chelator can be in a range of about 0.1 wt % to about 2.5 wt % of the total weight of active ingredients. For example, the insert may include disodium EDTA in a range of about 0.1 wt % to about 2.5 wt %.

The insert may include, in some embodiments, polyvinylpyrrolidone (PVP) as a stabilizer. PVP has been used as a dispersant for *Aloe vera* gel, gel concentrates, and gel extracts as well as for silver salt antimicrobial matrix products. The concentration of PVP can be in a range of about 0.6 wt % to about 2.5 wt % of the total weight of active ingredients.

In some embodiments, the insert may include non-ionic surfactants, such as polysorbates, which may act as a microbial membrane permeability enhancer. These polyoxymethylene derivatives are fatty acid esters of sorbitol copolymerized with ethylene oxide. Polysorbate 80 increases *Pseudomonas aeruginosa* cell permeability and increasing cell leakage. Polysorbate surfactants are currently used with multiple antimicrobial drugs to increase their pharmacologic activity. Polysorbate compounds used for this pad/insert include, but are not limited to, laurate ester; palmitate ester; mixture of stearate and palmitate ester; oleate ester; and combinations thereof. The concentration of polysorbate can be in a range of about 0.05 wt % to about 0.175 wt % of the total weight of active ingredients.

The insert may include, in some embodiments, allantoin (2,5-Dioxo-4-imidazolidinyl)urea. Allantoin has been approved as a skin protectant by the United States Food and Drug Administration. It currently is considered safe for use as an oral wound healing agent and in addition has a reported use in the treatment of burns as the silver salt. The concentration of allantoin can be in a range of about 0.1 wt % to about 1.5 wt % of the total weight of active ingredients.

In various embodiments, the insert may include humectants. Humectants are hygroscopic substances that serve dual purposes—they can both absorb moisture from a wound and provide moisture to a wound. If a wound is dry, a humectant substance will absorb moisture from the environment and sustain a moist environment for more optimal wound healing. If a wound is producing excess serous fluid, humectants aid in absorption of the excess fluid and help maintain a less moist, ideal wound environment. Suitable humectants include, without limitation, propylene glycol, panthenol, glycerol (e.g., glycerin), and combinations thereof. In addition to having humectant and moisturizing properties, panthenol is a precursor to vitamin B5, pantothenic acid, and is useful for synthesis of keratinocyte growth factor and fibroblast proliferation, which promotes optimal and accelerated wound healing. Glycerol is very hygroscopic making it ideal in the absorption or donation of moisture.

The insert may include, in some embodiments, nonionic water soluble polymers, which may act as binders, stabilizers, suspending agents, and thickeners. The nonionic water soluble polymers may act as the matrix for the hydrogel. These polymers are generally non-irritating and non-allergenic. Suitable examples of these polymers include, but are not limited to, hydroxyethyl cellulose, carboxymethylcellulose, hydroxypropyl cellulose, hypromellose, ethyl cellulose, their derivatives, or a combination thereof. Water-soluble linear polymers of both natural and synthetic origin are cross-linked to form hydrogels in a number of ways. Suitable methods of forming the hydrogels include, without limitation: linking polymer chains via chemical reaction; using ionizing radiation to generate main-chain free radicals which can recombine as cross-link junctions; or utilizing physical interactions such as entanglements, electrostatics, and crystallite formation. A variety of polymerization techniques can be used to form the hydrogels including bulk, solution, and suspension polymerization.

In some embodiments, the insert may include a buffering agent to achieve a pH appropriate for optimal wound healing. Suitable buffers include, but are not limited to, sodium hydroxide (NaOH), triethanolamine, tromethamine, or combinations thereof. The desired pH can be in a range of about 4 to about 7.4.

In some embodiments, the insert may include silver salts; allantoin, (2,5-Dioxo-4-imidazolidinyl)urea; purified water; humectants (such as propylene glycol, panthenol, and/or glycerin); polysorbates; tetra acetic acid; hydroxyethyl cellulose; ceratonia silique; sodium hydroxide (NaOH); acemannan (e.g., *Aloe Barbadensis—Aloe vera* gel); alpha-tocopheryl (Vitamin E); polyvinylpyrrolidone (PVP); and combinations thereof. The insert may provide radiation dermatitis therapy that is more effective against bacteria and *candida* as compared to, for example, silver salts alone or *Aloe vera* alone.

In an embodiment, the user may couple the inert to the garment. The insert may be initially sealed in a package. The insert may be used in a garment after radiation treatment, for example, overnight. A user may apply an insert multiple times a day for a predetermined period of time. For example, a user may apply an insert 3 times per day for 7 days. In some embodiments, the insert is reusable. For example, the same insert may be used over the course of three applications. A re-sealable bag may be used to store the insert when not being worn. For example, the insert may be stored in the refrigerator. The insert may be disposable.

It should be recognized that some embodiments may include other features. For example, while the garments 10, 30, 50 are not illustrated with lace or other ornamentation, such ornamentation may be included. Further, a garment may include a netting that could hold treatment creams against the skin. Alternatively, a wearer may place a treatment cream on the insert, inner layer, or more generally on the cup. Further, while the garments 10, 30, 50 are each illustrated as a bra, it will be recognized that embodiments may be directed to other garments including, for example, a camisole, an exercise top, a swim top, or a garment to be worn under sleepwear.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A garment for a wearer having breasts and an under bust located directly under the breasts, comprising:
   a head opening;
   first and second arm openings;
   a band configured to fit at the under bust of the wearer;
   a cup extending from the band comprising:
   an outer layer;
   an inner layer that is interior to the outer layer; and
   an attachment component configured to removably couple an insert to the inner layer; and
   the insert removably coupled to the inner layer, wherein the insert comprises a hydrogel, the hydrogel comprising a silver salt and acemannan;
   wherein, when the garment is worn, at least a portion of the insert is exposed to skin of the wearer, the insert providing topical therapy and cooling to the skin of the wearer,
   wherein the band is made from a material that includes holes, and
   wherein the outer layer is made from a material that includes holes.

2. The garment of claim 1, wherein the acemannan is provided in Aloe vera gel.

3. The garment of claim 1, wherein the silver salt comprises silver nitrate, silver dihydrogen citrate, silver citrate, silver chloride, silver benzoate, silver acetate, silver galacturonate, silver glucoronate, or a combination thereof.

4. The garment of claim 1, wherein the hydrogel further comprises a chelator, a stabilizer, a non-ionic surfactant, a skin protectant, a humectant, a nonionic water soluble polymer, a buffering agent, or a combination thereof.

5. The garment of claim 4, wherein the chelator comprises ethylenediaminetetraacetic acid (EDTA), ethylene glycol tetra acetic acid (EGTA), and 1,2-bis(o-aminophenoxy) ethane-N,N,N',N'-tetra acetic (BAPTA), or a combination thereof.

6. The garment of claim 4, wherein the stabilizer comprises polyvinylpyrrolidone.

7. The garment of claim 4, wherein the non-ionic surfactant comprises laurate ester, palmitate ester, stearate ester, oleate ester, or a combination thereof.

8. The garment of claim 4, wherein the skin protectant comprises allantoin.

9. The garment of claim 4, wherein the humectant comprises propylene glycol, panthenol, glycerol, or a combination thereof.

10. The garment of claim 4, wherein the nonionic water soluble polymer hydroxyethyl cellulose, carboxymethylcellulose, hydroxypropyl cellulose, hypromellose, ethyl cellulose, a derivative thereof, or a combination thereof.

11. The garment of claim 4, wherein the buffering agent comprises sodium hydroxide (NaOH), triethanolamine, tromethamine, or a combination thereof.

12. The garment of claim 4, wherein the hydrogel further comprises the chelator, the stabilizer, the non-ionic surfactant, the skin protectant, the humectant, the nonionic water soluble polymer, and the buffering agent.

13. The garment of claim 1, wherein the hydrogel comprises:
an ionic silver salt in a range of about 5 ppm to about 200 ppm;
anhydrous Aloe vera gel extract acemannan in a range of about 0.05 wt % to about 1 wt %;
disodium EDTA in a range of about 0.1 wt % to about 2.5 wt %;
polyvinylpyrrolidone in a range of about 0.6 wt % to about 2.5 wt %;
polysorbate in a range of about 0.05 wt % to about 0.175 wt %;
allantoin in a range of about 0.1 wt % to about 1.5 wt %; and
propylene glycol, panthenol, and glycerol.

14. The garment of claim 1, wherein a pH of the hydrogel is in a range of about 4 to about 7.4.

15. The garment of claim 1, wherein the band and the outer layer are made of hypoallergenic fabric.

16. The garment of claim 1, wherein the outer layer comprises about 10-30% polyamide and about 5-20% elastane.

17. The garment of claim 1, wherein a bottom edge of the inner layer extends along an outer surface of the band to a bottom edge of the cup to form a wireless support.

18. The garment of claim 1, wherein a bottom edge of the cup connects to the inner layer.

19. The garment of claim 1, wherein the holes in the material of the band and in the material of the outer layer are laser or die cut holes.

* * * * *